United States Patent [19]

Abe et al.

[11] Patent Number: 5,023,390

[45] Date of Patent: Jun. 11, 1991

[54] PROCESS FOR PRODUCTION OF 2,6-DIMETHYLNAPHTHALENE

[75] Inventors: Takafumi Abe; Shuji Ebata; Hiroshi Machida; Koichi Kida, all of Niigata, Japan

[73] Assignee: Mitsubishi Gas Chemical Company, Inc., Tokyo, Japan

[21] Appl. No.: 405,966

[22] Filed: Sep. 12, 1989

[30] Foreign Application Priority Data

Oct. 3, 1988 [JP] Japan .................................. 63-247372

[51] Int. Cl.$^5$ ....................... C07C 5/00; C07C 11/253; C07C 12/64; C07C 12/00

[52] U.S. Cl. .................... 585/320; 585/409; 585/410; 585/411; 549/242; 568/311; 568/814

[58] Field of Search ............... 585/320, 409, 410, 411; 549/242; 568/311, 814

[56] References Cited

U.S. PATENT DOCUMENTS

| | | | |
|---|---|---|---|
| 2,404,914 | 7/1946 | Mattox | 585/409 |
| 2,575,403 | 11/1951 | Young et al. | 568/814 |
| 2,802,812 | 8/1957 | Overberger | 568/814 |
| 3,931,348 | 1/1976 | Taniguchi et al. | 585/411 |

FOREIGN PATENT DOCUMENTS

| | | | |
|---|---|---|---|
| 50-000665 | 1/1975 | Japan | 585/411 |
| 50-001035 | 1/1975 | Japan | 585/409 |
| 50-012429 | 5/1975 | Japan | 585/411 |
| 50-017983 | 6/1975 | Japan | 585/411 |
| 50-022549 | 7/1975 | Japan | 585/411 |

Primary Examiner—H. M. S. Sneed
Assistant Examiner—J. Saba
Attorney, Agent, or Firm—Frishauf, Holtz, Goodman & Woodward

[57] ABSTRACT

A process for production of 2,6-dimethylnaphthalene is disclosed; comprising the steps: (1) an acylation step where 2,4-dimethylisobutyrophenone is produced from m-xylene, propylene and carbon monoxide: (2) a hydrogenation step where the carbonyl group of the above 2,4-dimethylisobutyrophenone is hydrogenated: and (3) a dehydrogenation and cyclization step where the above hydrogenated product is subjected to dehydrogenation and cyclization to produce the desired 2,6-dimethylnaphthalene. The process enables efficiently producing high quality or high purity 2,6-dimethylnaphthalene.

21 Claims, No Drawings

PROCESS FOR PRODUCTION OF 2,6-DIMETHYLNAPHTHALENE

BACKGROUND OF THE INVENTION

1. Field of the Invention

The present invention relates to a process for production of 2,6-dimethylnaphthalene and more particularly to a process for producing 2,6-dimethylnaphthalene on a commercial scale from m-xylene, propylene and carbon monoxide as starting materials through 2,4-dimethylisobutyrophenone.

2. Description of the Related Arts 2,6-Dimethylnaphthalene is generally used as a starting material for producing industrially useful 2,6-naphthalene dicarboxylic acid through oxidation. This 2,6-naphthalene dicarboxylic acid is used, for example, for producing polyethylene naphthalate fibers or films having excellent tensile strength and thermal resistance.

2,6-Dimethylnaphthalene which is such a useful chemical material, has heretofore been obtained by isolating it from a tar fraction. However, in this method of isolating from a tar fraction, only a small amount of 2,6-dimethylnaphthalene can be obtained and moreover its separation or purification is difficult. Thus this method using a tar fraction as a starting material cannot be said to be a method suitable for industrial production of 2,6-dimethylnaphthalene in large quantities and at low production costs.

In recent years, various methods of synthesizing 2,6-dimethylnaphthalene from various starting materials have been proposed. In fact, however, no industrial methods of production whereby 2,6-dimethylnaphthalene can be synthesized effectively and selectively from an inexpensive starting material have been developed.

For example, Japanese Patent Publication Nos. 17983/1975, 17984/1975 and 17985/1975 disclose methods in which 5-(o-tolyl)pentene-2 is used as a starting material and it is subjected to dehydrogenation and cyclization to produce 2,6-dimethylnaphthalene and other dimethylnaphthalene. In general, the 5-(tolyl)pentene-2 to be used as a starting material in the above methods is synthesized from o-xylene and 1,3-butadiene. In this reaction, however, alkylation of the methyl group in the o-xylene is unpractical and, therefore, the production of 5-(o-tolyl)pentene-2 itself is not easy. Also at the dehydrogenation and cyclization steps of 5-(o-tolyl)pentene-2, a number of dimethylnaphthalene isomers other than 2,6-dimethylnaphthalene are formed and, therefore, an isomerization step, and a complicated separation and purification step are required.

Japanese Patent Publication Nos. 1701/1976 and 5292/1978 disclose methods in which an alkylated product from toluene or p-xylene is used as a starting material and it is subjected to dehydrogenation and cyclization to produce various types of dimethylnaphthalenes as well as 2,6-dimethylnaphthalene. In particular, Japanese Patent Publication No. 5292/1978 discloses a method in which 3-methyl-4-(p-tolyl)-butane obtained by the side chain alkylation of p-xylene with butene-1 is used as a starting material and it is subjected to dehydrogenation and cyclization to produce 2,6-dimethylnaphthalene. However, since a large amount of an alkali metal such as sodium or potassium is generally used in the side chain alkylation, the starting material itself becomes expensive. Moreover, in the dehydrogenation and cyclization reaction of the starting material, a number of dimethylnaphthalene isomers other than 2,6-dimethylnaphthalene are also produced. Thus the above method cannot be said to be an industrially satisfactory method.

SUMMARY OF THE INVENTION

An object of the present invention is to provide a process for industrial production of 2,6-dimethylnaphthalene using inexpensive compounds as starting materials.

Another object of the present invention is to provide a process for efficiently producing high purity 2,6-dimethylnaphthalene not containing any isomers.

The present invention relates to a process for producing 2,6-dimethylnaphthalene which comprises the following three steps:

(1) an acylation step to synthesize 2,4-dimethylisobutyrophenone from m-xylene, propylene and carbon monoxide;

(2) a hydrogenation step to hydrogenate the carbonyl group of the above 2,4-dimethylisobutyrophenone; and (3) a dehydrogenation cyclization step to dehydrogenate and cyclize the hydrogenated product obtained in (2) above, thereby producing the desired 2,6-dimethylnaphthalene.

DESCRIPTION OF THE PREFERRED EMBODIMENTS

It will hereinafter be explained in detail how the present invention has been accomplished.

When m-xylene, propylene and carbon monoxide as starting materials were subjected to acylation in the presence of a Lewis acid catalyst, e.g., hydrogen fluoride, boron trifluoride or aluminum chloride, 2,4-dimethylisobutyrophenone was obtained selectively and in a high yield without substantially forming isomers, and the separation and recovery of the catalyst was possible.

The present inventors made extensive investigations to synthesize 2,6-dimethylnaphthalene from 2,4-dimethylisobutyrophenone. An attempt to synthesize 2,6-dimethylnaphthalene directly from 2,4-dimethylisobutyrophenone was made but with no success.

On the other hand, it has been found that if the carbonyl group of 2,4-dimethylisobutyrophenone is hydrogenated to produce 1-(2,4-dimethylphenyl)-isobutyl alcohol, 1-(2,4-dimethylphenyl)-2-methylpropane and 1-(2,4-dimethylphenyl)-2-methyl-propene, and then each of the compounds or a mixture thereof is subjected to a dehydrogenation and cyclization reaction, 2,6-dimethylnaphthalene can be obtained in a high yield.

In the hydrogenation reaction of 2,4-dimethylisobutyrophenone, it is preferred that 2,4-dimethylisobutyrophenone is converted into 1-(2,4-dimethylphenyl)-2-methyl-propene because it requires a very small amount of hydrogen for production thereof among the above three hydrogenated products. Moreover when 1-(2,4-dimethylphenyl)-2-methyl-propene was subjected to dehydrogenation and cyclization reactions, 2,6-dimethylnaphthalene could be obtained in the highest yield.

This 1-(2,4-dimethylphenyl)-2-methyl-propene contains 1-propene and 2-propene. In order to produce mainly 1-(2,4-dimethylphenyl)-2-methyl-propene, it is preferred that 1-(2,4-dimethylphenyl)-isobutyl alcohol is selectively formed in the hydrogenation of 2,4-dimethylisobutyrophenone, and then subjected to the dehydration reaction.

The scheme of reaction which occurs in the process of the present invention is shown below for easier understanding thereof.

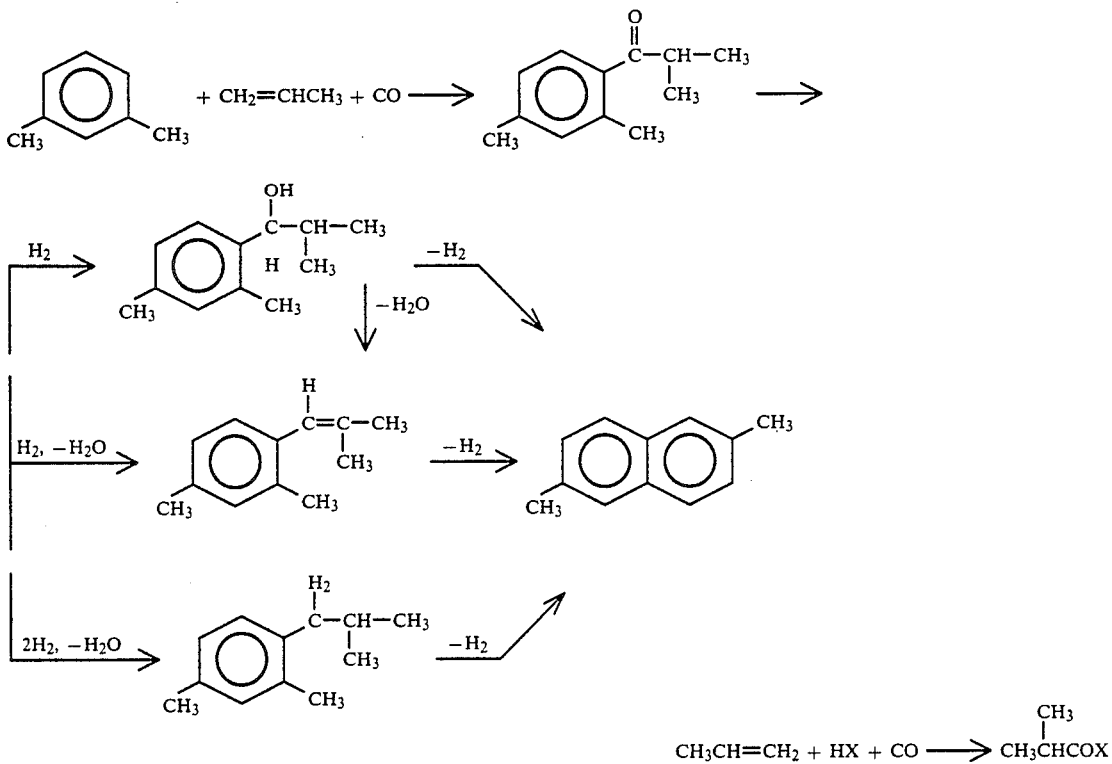

2,6-Dimethylnaphthalene produced by the process of the present invention contains almost no isomers. Thus neither an isomerization step nor a complicated separation step is required, and high purity 2,6-dimethylnaphthalene can be easily obtained by the usual operations such as distillation and recrystallization.

Each step of the process of the present invention will hereinafter be explained in detail.

Acylation Step

Predetermined amounts of anhydrous hydrogen halide (HF, HCl or HBr) and a Lewis acid catalyst (BF$_3$ or AlCl$_3$) are placed in an anticorrosive (SUS-316 or Hastelloy C) autoclave, and then carbon monoxide is introduced under a pressure of 1 to 150 kg/cm$^2$, preferably 10 to 80 kg/cm$^2$. The temperature is chosen within the range of 0° to 100° C. and preferably 10° to 60° C. Then propylene or 2-halopropane formed according to the formula (1):

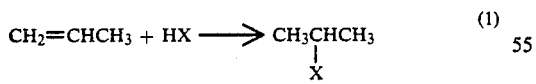

(wherein X is F, Cl or Br) is continuously introduced.

In the practice of the reaction, it is necessary that the reaction system is stirred, thereby sufficiently contacting liquid and gas.

In connection with propylene and carbon monoxide to be used in the reaction, high purity is preferable, and it is desirable that water, carbon dioxide, etc. should be removed to the utmost.

The reaction of the present invention proceeds according to the route represented by the following formula (2) or (3):

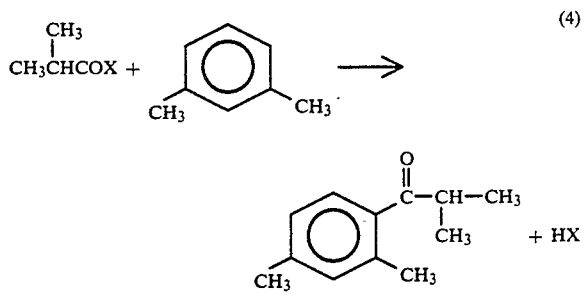

(wherein X is the same defined above), and isobutyryl halide results.

After removal of carbon monoxide from the reaction system, a Lewis acid, e.g., AlCl$_3$, BF$_3$, BCl$_3$ or SbF$_5$ is added to the reaction product solution to prepare a reaction Xylene is introduced while stirring into the above mixture, and is reacted therewith.

The reaction proceeds as shown in the following formula (4):

(4)

CH$_3$CHCOX + [xylene] →
    |
    CH$_3$

[product] + HX

In the reaction, the temperature is −10° to 60° C. and preferably 0° to 40° C., and the reaction is completed in a residence time of 15 to 180 minutes.

The acylation reaction in the process of the present invention comprises a series of reaction steps as described above. The formulae (1), (3) and (4) or the formulae (2) and (4) can be summarized as shown by the formula (5):

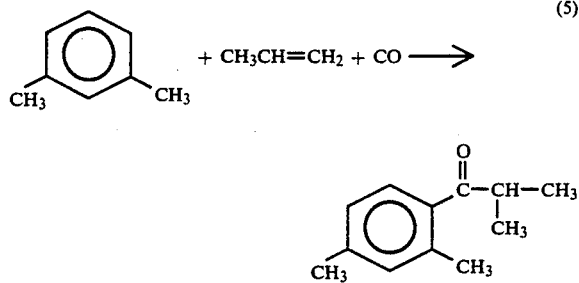

(5)

The acylation reaction can be carried out batchwise or continuously. Separation of the catalyst from the reaction product is usually carried out by a phase separation method or a thermal decomposition method.

Hydrogenation Step

Hydrogenation of 2,4-dimethylisobutyrophenone obtained at the acylation step can be carried out by various methods. In practice, 2,4-dimethylisobutyrophenone is contacted with hydrogen in a liquid phase in the presence of a solid catalyst.

As the catalyst; a Raney type catalyst such as Raney nickel or Raney cobalt, a copper chrominum-base catalyst, a metal oxide catalyst such as a nickel oxide catalyst or a cobalt oxide catalyst, or a noble metal catalyst comprising alumina or active carbon with a noble metal such as platinum or palladium deposited thereon, is effectively used.

In practice of the hydrogenation reaction, the type of the catalyst and the reaction conditions are determined depending on the desired hydrogenated product. In general, the hydrogen pressure is 1 to 100 $kg/cm^2$ and preferably 5 to 50 $kg/cm^2$, and the reaction temperature is 30° to 300° C. and preferably 60° to 200° C.

The hydrogenation reaction can be carried out batchwise or continuously. In practice, a trickle type reaction system using a fixed bed catalyst is usually employed.

Dehydration Step 1-(2,4-Dimethylphenyl)-2-methyl-propene can be produced even by hydrogenation and dehydration of 2,4-dimethylisobutyrophenone. Rather it is easily obtained by a dehydration reaction of 1-(2,4-dimethylphenyl)-isobutyl alcohol.

This dehydration reaction is carried out by a gas phase reaction using a catalyst such as active alumina or silica alumina. The reaction temperature is 200° to 400° C. and preferably 250° to 350° C., and 1-(2,4-dimethylphenyl)-2-methyl-propene can be obtained in a high yield.

Dehydrogenation and Cyclization Step 2,6-Dimethylnaphthalene can be produced from any of 1-(2,4-dimethylphenyl)-isobutyl alcohol, 1-(2,4-dimethylphenyl)-2-methyl-propene and 1-(2,4-dimethylphenyl)-2-methyl-propane by a dehydrogenation and cyclization reaction. The dehydrogenation and cyclization reaction is carried out by contacting the starting material with a solid catalyst in a gas phase at an elevated temperature.

As the catalyst, a metal oxide catalyst such as an alumina chromia catalyst or an iron oxide catalyst, or a catalyst comprising alumina or active carbon with a noble metal such as platinum or palladium deposited thereon is suitably used.

The reaction temperature is 350° to 700° C. and preferably 450° to 600° C.

The reaction pressure is not critical and the reaction can be carried out under reduced pressure, atmospheric pressure, or high pressure. The reaction is usually carried out in the range of atmospheric pressure to 2 $kg/cm^2$.

As the reaction type; a fixed bed adiabatic type, a fixed bed shell and tube type, or a fluid bed type is employed.

The reaction mixture obtained at the cyclization and dehydrogenation step contains, as well as the objective 2,6-dimethylnaphthalene not containing isomers, unreacted starting materials and by-products such as β-methylnaphthalene and pseudocumene.

A high purity 2,6-dimethylnaphthalene product can be easily obtained by distillation or recrystallization of the above reaction mixture. Unreacted starting materials recovered are re-used in the reaction.

In accordance with the process of the present invention, high purity 2,6-dimethylnaphthalene not containing isomers can be produced from m-xylene, propylene and carbon monoxide as starting materials through the 2,4-dimethylisobutyrophenone formed. Thus the process of the present invention is of high industrial significance as a method for inexpensively producing high purity 2,6-dimethylnaphthalene.

The present invention is described in greater detail with reference to the following examples.

EXAMPLE

(1) Acylation Step

Sixty grams of HF and 2.1 g of $BF_3$ were placed in a 100-ml autoclave (Hastelloy C), and CO was introduced until pressure reached 20 $kg/cm^2G$. While vigorous stirring, 16.8 g of propylene was continuously introduced thereto over 30 minutes.

The reaction temperature was maintained at 30° C., and the pressure in the system was maintained at 20 $kg/cm^2G$ by compensating for the absorbed CO. After completion of CO absorption; the reaction mixture was cooled and the remaining CO was purged.

Then, 17.7 g of fresh $BF_3$ was added again to adjust the catalyst ratio. The reaction temperature was maintained at 5° C., and 23.4 g of m-xylene was introduced while stirring over 15 minutes. Then the reaction temperature was raised to 25° C. and stirring was continued for 30 minutes to complete the reaction.

The yield of 2,4-dimethylisobutyrophenone was 95% based on the weight of m-xylene.

(2) Hydrogenation Step

A SUS 316 reactor (diameter: 15 mm; length: 300 mm) was packed with 36 g of a copper chromite catalyst (N-201 catalyst produced by Nikki Chemical Co., Ltd.). According to a trickel type reaction system, a starting material of 2,4-dimethylisobutyrophenone was introduced into a catalyst layer through a preheating layer at a rate of 18 g/hr under a hydrogen pressure of 6 $kg/cm^2G$ at a catalyst layer temperature of 150° C.

An analysis of the reaction mixture showed that the conversion of 2,4-dimethylisobutyrophenone was 97% and the selectivity to 1-(2,4-dimethylphenyl)-isobutyl alcohol was 98%.

(3) Dehydration Step

The 1-(2,4-dimethylphenyl)-isobutyl alcohol as obtained above was used as a starting material and reacted as follows:

A heat-resistant glass (Pyrex glass) reaction tube (diameter: 15 mm; length: 300 mm) was packed with 15 g of active alumina (Neobead GB produced by Mizusawa Kagaku Co., Ltd.). The catalyst layer temperature was maintained at 300° C., and the 1-(2,4-dimethylpheyl)-isobutyl alcohol as starting material was introduced in admixture with a small amount of $N_2$ gas into a catalyst layer through a preheating layer at a rate of 15 g/hr.

An analysis of the reaction mixture showed that the conversion of 1-(2,4-dimethylphenyl)-isobutyl alcohol was 100%, and the selectivity to 1-(2,4-dimethyphenyl)-2-methyl-propene was 99%.

(4) Dehydrogenation and Cyclization Step

A quartz glass reaction tube (diameter: 12 mm; length: 300 mm) was packed with 10 g of a 10% $Cr_2O_3$-5% $K_2O$—$Al_2O_3$ catalyst, and the catalyst layer was maintained at 530° C.

A 10% solution of 1-(2,4-dimentylphenyl)-2-methyl-propene dissolved in toluene was vaporized by passing through a preheating layer at a rate of 10 g/hr and introduced into the catalyst layer in admixture with 30 ml/minute of $N_2$ gas.

An analysis of the reaction mixture showed that the conversion of 1-(2,4-dimethylphenyl)-2-methyl-propene was 89% and the selectivity to 2,6-dimethylnaphthalene was 62%.

What is claimed is:

1. A process for producing 2,6-dimethylnaphthalene which comprises (1) an acylation step comprising reacting m-xylene, propylene and carbon monoxide to form 2,4-dimethylisobutyrophenone; (2) a hydrogenation step comprising hydrogenating the carbonyl group of said 2,4-dimethylisobutyrophenone; and (3) a dehydrogenation and cyclization step comprising dehydrogenating and cyclizing said hydrogenated product of step 2 to form 2,6-dimethylnaphthalene.

2. A process for producing 2,6-dimethylnaphthalene which comprises (1) an acylation step comprising reacting m-xylene, propylene and carbon monoxide to form 2,4-dimethylisobutyrophenone; (2) a hydrogenation step comprising hydrogenating the carbonyl group of said 2,4-dimethylisobutyrophenone to produce 1-(2,4-dimethylphenyl)-isobutyl alcohol: (3) a dehydrogenation step comprising dehydrating said 1-(2,4-dimethylphenyl)-isobutyl alcohol to produce 1-(2,4-dimethylphenyl)-2-methyl-propene; and (4) a dehydrogenation and cyclization step comprising dehydrogenating and cyclizing said 1-(2,4-dimethylphenyl)-2-methyl-propene to form 2,6-dimethylnaphthalene.

3. The process as claimed in claim 1 wherein the hydrogenated product obtained at the hydrogenation step (2) is 1-(2,4-dimethylphenyl)-isobutyl alcohol.

4. The process as claimed in claim 1 wherein the hydrogenated product obtained at the hydrogenation step (2) is 1-(2,4-dimethylphenyl)-2-methylpropane.

5. The process as claimed in claim 1 wherein the hydrogenated product obtained at the hydrogenation step (2) is 1-(2,4-dimethylphenyl)-2-methyl-propene.

6. The process as claimed in claim 1 wherein the hydrogenated product obtained at the hydrogenation step (2) is a mixture of 1-(2,4-dimethylphenyl)-isobutyl alcohol, 1-(2,4-dimethylphenyl)-2-methylpropane and 1-(2,4-dimethylphenyl)-2-methyl-propene.

7. The process as claimed in claim 1 wherein the reaction at the acylation step (1) is carried out in the presence of a Lewis acid.

8. The process as claimed in claim 1 wherein the reaction at the hydrogenation step (2) is carried out in the presence of a solid catalyst.

9. The process as claimed in claim 8 wherein the solid catalyst is a Raney catalyst, a copper chrominum catalyst, a metal oxide catalyst or a noble metal catalyst.

10. The process as claimed in claim 1 wherein the reaction at the dehydrogenation and cyclization step (3) is carried out in the presence of a solid catalyst.

11. The process as claimed in claim 10 wherein the solid catalyst is an alumina chromia catalyst, a metal oxide catalyst or a noble metal catalyst.

12. The process as claimed in claim 2 wherein the reaction at the dehydration step (3) is carried out in the presence of a catalyst.

13. The process as claimed in claim 12 wherein the catalyst is active alumina or silica alumina.

14. The process as claimed in claim 1 wherein
    the acylation step (1) is carried out in the presence of a Lewis acid;
    the hydrogenation step (2) is carried out in the presence of a solid catalyst; and
    the dehydrogenation and cyclization step (3) is carried out in the presence of a solid catalyst.

15. The process as claimed in claim 14 wherein said solid catalyst used in said hydrogenation step (2) is a Raney catalyst, a copper chromium catalyst, a metal oxide catalyst or a noble metal catalyst; and wherein said solid catalyst used in said dehydrogenation and cyclization step (3) is an alumina chromia catalyst, a metal oxide catalyst or a noble metal catalyst.

16. The process as claimed in claim 15 wherein the hydrogenated product at the hydrogenation step (2) is a mixture of 1-(2,4-dimethylphenyl)-isobutyl alcohol, 1-(2,4-dimethylphenyl)-2-methylpropane and 1-(2,4-dimethylphenyl)-2-methyl-propene.

17. The process as claimed in claim 12 wherein
    the acylation step (1) is carried out in the presence of a Lewis acid;
    the hydrogenation step (2) is carried out in the presence of a solid catalyst; and
    the dehydrogenation and cyclization step (4) is carried out in the presence of a solid catalyst.

18. The process as claimed in claim 17 wherein said solid catalyst used in said hydrogenation step (2) is a Raney catalyst, a copper chromium catalyst, a metal oxide catalyst or a noble metal catalyst; wherein said catalyst used in said dehydration step (3) is active alumina or silica alumina; and wherein said solid catalyst used in said dehydrogenation and cyclization step (4) is an alumina chromia catalyst, a metal oxide catalyst or a noble metal catalyst.

19. The process of claim 17 wherein carbon monoxide, m-xylene and propylene are acylated in the presence of HF and $BF_3$ to produce 2,4-dimethylisobutyrophenone which was then hydrogenated in the presence of a copper chromite catalyst to produce 1-(2,4-dimethylphenyl)-isobutyl alcohol which was then heated in contact with active alumina to produce 1-(2,4-dimethylphenyl)-2-methylpropene which was dissolved in a solvent and vaporized and contacted with a $Cr_2O_3$—$K_2O$—$Al_2O_3$ catalyst to form 2,6-dimethylnaphthalene.

20. The process of claim 18 wherein said hydrogenation step (1) is carried out in the presence of (i) anhydrous HF, HCl or HBr and (ii) $BF_3$ or $AlCl_3$.

21. The process of claim 15 wherein said hydrogenation step (1) is carried out in the presence of (i) anhydrous HF, HCl or HBr and (ii) $BF_3$ or $AlCl_3$.

* * * * *